United States Patent
Ebert et al.

(10) Patent No.: US 11,236,034 B2
(45) Date of Patent: *Feb. 1, 2022

(54) METHOD FOR PREPARING ACRYLIC ACID

(71) Applicant: Rohm and Haas Company, Collegeville, PA (US)

(72) Inventors: Donald A. Ebert, Friendswood, TX (US); Timothy Allen Hale, Marshall, NC (US); Brian Robert Keyes, Houston, TX (US); Justin Rose, Marvel, TX (US); Jinsuo Xu, Berwyn, PA (US)

(73) Assignee: Rohm and Haas Company, Collegeville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/980,936

(22) PCT Filed: Feb. 21, 2019

(86) PCT No.: PCT/US2019/018876
§ 371 (c)(1),
(2) Date: Sep. 15, 2020

(87) PCT Pub. No.: WO2019/182713
PCT Pub. Date: Sep. 26, 2019

(65) Prior Publication Data
US 2020/0407306 A1  Dec. 31, 2020

Related U.S. Application Data

(60) Provisional application No. 62/645,860, filed on Mar. 21, 2018.

(51) Int. Cl.
*C07C 51/25* (2006.01)
*C07C 57/04* (2006.01)

(52) U.S. Cl.
CPC .......... *C07C 51/252* (2013.01); *C07C 57/04* (2013.01)

(58) Field of Classification Search
CPC ....... C07C 51/252; C07C 45/35; C07C 57/04; C07C 47/22
See application file for complete search history.

(56) References Cited

U.S. PATENT DOCUMENTS

| | | | |
|---|---|---|---|
| 4,697,027 A | 9/1987 | Sugihara et al. | |
| 4,732,996 A | 3/1988 | Moorhead et al. | |
| 4,892,856 A | 1/1990 | Kawajiri et al. | |
| 5,104,999 A | 4/1992 | Satoh | |
| 5,210,254 A | 5/1993 | Ritscher et al. | |
| 5,247,117 A | 9/1993 | Yamazaki et al. | |
| 5,446,185 A | 8/1995 | Cobb et al. | |
| 5,914,421 A | 6/1999 | Bank et al. | |
| 6,028,220 A | 2/2000 | Wada et al. | |
| 6,127,505 A | 10/2000 | Slagel | |
| 6,150,551 A | 11/2000 | Kropfgans et al. | |
| 6,175,031 B1 | 1/2001 | Tachikawa | |
| 6,235,832 B1 | 5/2001 | Deng et al. | |
| 6,265,518 B1 | 7/2001 | Krahnke et al. | |
| 6,639,106 B1 * | 10/2003 | Elder | C07C 51/252 562/532 |
| 6,762,148 B2 | 7/2004 | Ohishi et al. | |
| 8,242,376 B2 | 8/2012 | Lauffer et al. | |
| 9,205,414 B2 | 12/2015 | Kawano et al. | |
| 9,822,051 B2 | 11/2017 | Steffan et al. | |
| 2004/0055970 A1 * | 3/2004 | Matsumoto | C02F 1/727 210/761 |
| 2005/0272952 A1 * | 12/2005 | Cremer | C07C 57/04 562/545 |
| 2009/0030230 A1 | 1/2009 | Fischer et al. | |
| 2009/0270646 A1 | 10/2009 | Ferguson et al. | |
| 2010/0005721 A1 * | 1/2010 | Houtekamer | C10L 3/10 48/127.3 |
| 2014/0024849 A1 | 1/2014 | Standke et al. | |

FOREIGN PATENT DOCUMENTS

| | | |
|---|---|---|
| EP | 0293224 | 11/1988 |
| EP | 1452227 | 9/2004 |
| GB | 1115052 | 5/1968 |
| JP | 2003064085 | 3/2003 |
| JP | 2014224068 | 12/2014 |
| RU | 2537302 | 12/2014 |

* cited by examiner

*Primary Examiner* — Yevgeny Valenrod
*Assistant Examiner* — Blaine G Doletski
(74) *Attorney, Agent, or Firm* — Brian L. Mutschler

(57) ABSTRACT

Provided is a process for preparing acrylic acid comprising (1) preparing acrolein by catalytic gas phase oxidation comprising (a) providing a reaction gas comprising (i) 5 to 10 mol % propylene, (ii) 0.02 to 0.75 mol % propane, and (iii) 0.25 to 1.9 mol % of a fuel mixture comprising at least one of methane and ethane, wherein the molar ratio of the total amount of propane, methane, and ethane to the total amount of propylene is from 0.01:1 to 0.25:1, (b) contacting the reaction gas with a first mixed metal oxide catalyst to form a mixture comprising acrolein, wherein the first mixed metal oxide catalyst comprises one or more of molybdenum, bismuth, cobalt, and iron, and (2) contacting the acrolein mixture with a second mixed metal oxide catalyst to form a mixture comprising acrylic acid, wherein the second mixed metal oxide catalyst comprises one or more of molybdenum, vanadium, tungsten, copper, and antimony.

10 Claims, No Drawings

METHOD FOR PREPARING ACRYLIC ACID

FIELD OF THE INVENTION

This invention relates generally to a method for preparing acrylic acid by catalytic gas phase oxidation. The method includes providing a reaction gas containing propylene, propane, and a fuel mixtures of at least one of methane and ethane, and contacting it with a first oxidation catalyst to form a mixture containing acrolein, and contacting the acrolein mixture with a second oxidation catalyst to form a mixture containing acrylic acid.

BACKGROUND

Acrylic acid can be produced commercially by selective oxidation of acrolein, which can be produced by selective oxidation of propylene. Commercially available propylene can be divided into different grades based on the levels of other impurities, e.g., refinery grade, chemical grade, and polymer grade. Depending on the price differential, there can be an advantage to using one grade over the other. While different grades of propylene can be used as a feed in producing acrolein via catalytic oxidation, changing the propylene grade from one to another can have a significant impact on the fuel content of the absorber off gas, and can also be prohibitive due to the fact that acrolein plants are typically designed for a fixed propylene composition. For example, an existing plant designed for Chemical Grade Propylene (containing 3 to 7% by volume propane as the main impurity) faces a few challenges with high purity Polymer Grade Propylene (containing less than 0.5% by volume propane as the main impurity): (1) a shortage of propane fuel (an impurity in the propylene) that is used as a fuel for downstream thermal oxidation of volatile organics prior to venting into the atmosphere; and (2) a shortage of propane as a ballast gas that moves the reactor feed composition away from the flammable region.

Different propylene grades used as a feed gas for producing acrolein have been utilized in the art. For example, WO 2014/195157 A1 discloses a method of producing acrolein with feed gas containing Refinery Grade Propylene and a specified range of sulfur and unsaturated hydrocarbons. The prior art does not, however, disclose a method for preparing acrolein via gas phase oxidation by providing a reaction gas according to the present invention which allows for the use of a high grade of propylene in the reactor feed gas for an existing plant designed for Chemical Grade Propylene without sacrificing production rate or requiring other capital improvements.

Accordingly, there is a need to develop a method that allows for the use of a reactor feed gas containing a high grade of propylene, while not suffering from the drawbacks of the shortage of fuel for downstream thermal oxidation of volatile organics, and shortage of a ballast gas that moves the reactor feed composition away from the flammable region.

STATEMENT OF INVENTION

One aspect of the invention provides a process for preparing acrylic acid comprising (1) preparing acrolein by catalytic gas phase oxidation comprising (a) providing a reaction gas comprising (i) 5 to 10 mol % propylene, (ii) 0.02 to 0.75 mol % propane, and (iii) 0.25 to 1.9 mol % of a fuel mixture comprising at least one of methane and ethane, wherein the molar ratio of the total amount of propane, methane, and ethane to the total amount of propylene is from 0.01:1 to 0.25:1, (b) contacting the reaction gas with a first mixed metal oxide catalyst to form a mixture comprising acrolein, wherein the first mixed metal oxide catalyst comprises one or more of molybdenum, bismuth, cobalt, and iron, and (2) contacting the acrolein mixture with a second mixed metal oxide catalyst to form a mixture comprising acrylic acid, wherein the second mixed metal oxide catalyst comprises one or more of molybdenum, vanadium, tungsten, copper, and antimony.

Another aspect of the invention provides process for preparing acrylic acid comprising (1) preparing acrolein by catalytic gas phase oxidation comprising (a) providing a reaction gas comprising (i) 7.5 to 8.2 mol % propylene, (ii) 0.03 to 0.62 mol % propane, and (iii) 0.5 to 1.4 mol % of a fuel mixture comprising at least one of methane and ethane, wherein the fuel mixture comprises sulfur in an amount of less than 30 parts per million by volume of the fuel mixture, wherein the molar ratio of the total amount of propane, methane, and ethane to the total amount of propylene is from 0.1:1 to 0.18:1, and (b) contacting the reaction gas with a first mixed metal oxide catalyst to form a mixture comprising acrolein, wherein the oxidation catalyst comprises a first mixed metal oxide catalyst comprising a primary component selected from the group consisting of molybdenum, bismuth, and combinations thereof, and a secondary component selected from the group consisting of cobalt, iron, nickel, zinc, tungsten, phosphorous, manganese, potassium, magnesium, silicon, aluminum, and combinations thereof, wherein the primary component and secondary component are in an atomic ratio of from 9:28 to 28:9, and (2) contacting the acrolein mixture with a second mixed metal oxide catalyst to form a mixture comprising acrylic acid, wherein the second mixed metal oxide catalyst comprises a primary component selected from the group consisting of molybdenum, vanadium, and combinations thereof, and a secondary component selected from the group consisting of tungsten, cobalt, copper, and combinations thereof, wherein the primary component and secondary component are in an atomic ratio of from 1:1 to 11:1.

DETAILED DESCRIPTION

The inventors have now surprisingly found that acrylic acid can be prepared from acrolein prepared by catalytic gas phase oxidation of a reaction gas containing a high grade propylene while avoiding the shortage of fuel for downstream thermal oxidation of volatile organics, and the shortage of ballast gas that moves the reactor feed composition away from the flammable region. Such drawbacks are avoided by including a fuel mixture comprising at least one of methane and ethane as a supplement to avoid the effects that would otherwise result from using high grades of propylene containing relatively lower amounts of propane as an impurity. Accordingly, the present invention provides in one aspect a process for preparing acrylic acid comprising (1) preparing acrolein by catalytic gas phase oxidation comprising (a) providing a reaction gas comprising (i) 5 to 10 mol % propylene, (ii) 0.02 to 0.75 mol % propane, and (iii) 0.25 to 1.9 mol % of a fuel mixture comprising at least one of methane and ethane, wherein the molar ratio of the total amount of propane, methane, and ethane to the total amount of propylene is from 0.01:1 to 0.25:1, (b) contacting the reaction gas with a first mixed metal oxide catalyst to form a mixture comprising acrolein, wherein the first mixed metal oxide catalyst comprises one or more of molybdenum, bismuth, cobalt, and iron, and (2) contacting the acrolein mixture with a second mixed metal oxide catalyst, wherein the second mixed metal oxide catalyst comprises one or more of molybdenum, vanadium, tungsten, copper, and antimony.

The inventive process comprises providing a reaction gas that is contacted with an oxidation catalyst to form a mixture containing acrolein. The reaction gas contains propylene, propane, and a fuel mixture containing at least one of methane and ethane. The reaction gas contains propylene in an amount of from 5 to 10 mol %, preferably from 6.5 to 9 mol %, and more preferably from 7.5 to 8.2 mol %, based on the total volume of the reaction gas. The reaction gas contains propane in an amount of from 0.02 to 0.75 mol %, preferably from 0.02 to 0.65 mol %, and more preferably from 0.03 to 0.62 mol %, based on the total volume of the reaction gas. The reaction gas contains a fuel mixture containing at least one of methane and ethane in an amount of from 0.25 to 1.9 mol %, preferably from 0.4 to 1.6 mol %, and more preferably of from 0.5 to 1.4, based on the total volume of the reaction gas. In certain embodiments, the reaction gas contains methane in an amount of from 0.5 to 1.9 mol %, preferably from 0.8 to 1.6 mol %, and more preferably of from 1.1 to 1.4 mol %, based on the total volume of the reaction gas. In certain embodiments, the molar ratio of the total amount of propane, methane, and ethane in the reaction gas to the total amount of propylene in the reaction gas is from 0.1:1 to 0.25:1, preferably from 0.1:1 to 0.2:1, and more preferably from 0.1:1 to 0.18:1.

The reaction gas further contains an oxidant for the oxidation of propylene to acrolein, and acrolein to acrylic acid. Suitable oxidants include, for example, oxygen ($O_2$). Suitable sources of oxygen include, for example, air or a source that contains a higher purity of $O_2$. In certain embodiments, the molar ratio of $O_2$ to propylene is in the range of from 1.6:2.2, preferably from 1.7:2.0.

The reaction gas of the inventive process is contacted with an oxidation catalyst—a first mixed metal oxide catalyst. Mixed metal oxides catalysts that are known in the art, e.g., as described in U.S. Pat. Nos. 6,028,220, 8,242,376, and 9,205,414. Suitable first mixed metal oxide catalysts include, for example, those including one more of molybdenum, bismuth, cobalt, iron, nickel, zinc, tungsten, phosphorous, manganese, potassium, magnesium, silicon, and aluminum. In certain embodiments, the first mixed metal oxide catalyst comprises one or more of molybdenum, bismuth, cobalt, and iron. In certain embodiments, the first mixed metal oxide catalyst comprises primary and secondary components in an atomic ratio of from 9:28 to 28:9, preferably from 11:28 to 20:9, and more preferably of from 13:28 to 14:9. In certain embodiments, the primary component comprises one or more of molybdenum and bismuth. In certain embodiments, the secondary component comprises one or more of cobalt, iron, nickel, zinc, tungsten, phosphorous, manganese, potassium, magnesium, silicon, and aluminum.

In certain embodiments, the fuel mixture contains methane that is sourced from natural gas that includes impurities that are detrimental to the oxidation catalyst, e.g., catalyst poisons such as various sulfur compound (e.g., $H_2S$, dimethyl sulfide, carbonyl sulfide, mercaptans, and the like). Gas containing such catalyst poisons are known in the art as "sour gas." Sour gas can be "sweetened" by removing such sulfur compounds from the natural gas. Sulfur compounds can be removed it their presence has negative impacts on the catalyst performance, or downstream thermal oxidizer. Suitable sulfur removal technologies are known in the art and include, for example, by flowing the natural gas through a fixed bed packed with absorbent materials. In certain embodiments, the fuel mixture contains sulfur in an amount of less than 30 parts per million by volume of the fuel mixture, preferably less than 5 parts per million, more preferably less than 1 part per million, and even more preferably less than 0.1 part per million, by volume of the fuel mixture.

In certain embodiments, the inventive process step of contacting the reaction gas to form a mixture comprising acrolein comprises passing the reaction gas through a reactor tube or through a plurality of reactor tubes in parallel, each of which is filled with the first mixed metal oxide catalyst. In certain embodiments, the one or more reactor tubes are charged with the first mixed metal oxide catalyst to a length of from 1 to 7 meters, preferably from 2 to 6 meters, and more preferably of from 3 to 5 meters. In certain embodiments, the internal diameter of each reactor tube is in the range of from 15 to 50 mm, preferably 20 to 45 mm, and more preferably of from 22 to 40 mm.

The preparation of acrylic acid further comprises contacting the acrolein mixture obtained by the inventive process described above with a mixture of oxidation catalysts—the first mixed metal oxide catalyst described above and a second mixed metal oxide catalyst to produce a mixture containing acrylic acid. Suitable second mixed metal oxide catalysts are known in the art, e.g., as described in U.S. Pat. Nos. 4,892,856 and 6,762,148, and include, for example, one or more of molybdenum, vanadium, tungsten, copper, and antimony. In certain embodiments, the second mixed metal oxide catalyst comprises primary and secondary components in an atomic ratio of from 1:1 to 11:1, preferably from 2:1 to 9:1, and more preferably of from 3:1 to 7:1. In certain embodiments, the primary component comprises one or more of molybdenum and vanadium. In certain embodiments, the secondary component comprises one or more of tungsten, copper, and antimony.

In certain embodiments, the inventive process step of contacting the reaction gas to form a mixture comprising acrolein comprises passing the reaction gas through a reactor tube or through a plurality of reactor tubes in parallel, each of which is filled with a mixture of the first mixed metal oxide catalyst and the second mixed metal oxide catalyst. In certain embodiments, the one or more reactor tubes are charged with mixed metal oxide catalysts to a length of from 1 to 7 meters, preferably from 2 to 6 meters, and more preferably of from 3 to 5 meters. In certain embodiments, the internal diameter of each reactor tube is in the range of from 15 to 50 mm, preferably 20 to 45 mm, and more preferably of from 22 to 40 mm.

Some embodiments of the invention will now be described in detail in the following Examples.

EXAMPLES

Example 1

Characterization of Thermal Oxidation Constraints on Exemplary and Comparative Processes A conventional two stage single pass acrylic acid process is operated with typical conditions on Chemical Grade Propylene ("CGP"), Polymer Grade Propylene ("PGP"), and PGP with supplemental fuel, as recited in Table 1.

TABLE 1

Thermal Oxidation Constraints on Exemplary and Comparative Processes

|  | Operation w/CGP | Operation w/PGP | Operation w/PGP + fuel injection |
|---|---|---|---|
| Relative $C_3H_6$ Rate (% of maximum) | 100 | 72 | 100 |
| $C_3H_6$ Purity (mol %) | 94.50 | 99.50 | 99.50 |
| $C_3H_6$ Concentration (mol %) | 8.0 | 8.0 | 8.0 |
| $C_3H_8$ Concentration (mol %) | 0.47 | 0.04 | 0.05 |
| Supplemental $C_1$-$C_3$ Fuel Concentration (mol %) | 0.00 | 0.00 | 1.07 |
| Total $C_1$-$C_3$ Fuel Concentration (mol %) | 0.47 | 0.04 | 1.11 |
| $C_3H_6$ Conversion (%) | 96.0 | 96.0 | 96.0 |
| Residual Acrolein Yield (%) | 0.50 | 0.50 | 0.50 |
| Total $C_1$-$C_3$ fuel:propylene (mol ratio) | 0.058 | 0.005 | 0.139 |
| AOG[+] Heating Value (Btu/SCF) | 33 | 18 | 33 |
| Thermal Oxidizer Firebox Temperature (° C.) | 965 | 964 | 965 |
| Stack $O_2$ (mol %) | 2.95 | 2.94 | 2.94 |
| Tox Burner Capacity (%) | 100 | 100 | 100 |

[+]"AOG" represents the Absorber Off Gas

The results demonstrate that the process is constrained by energy input to the thermal oxidizer. Operation with the above conditions results in a vapor waste stream containing 30 to 40% of the energy input to the thermal oxidizer. As the purity of the propylene feedstock increases, the energy content in the vapor waste stream decreases. At the extreme case of a polymer grade propylene feed with propylene 99.5% minimum, the energy content in the vapor waste stream is 50% of what it was with CGP. Without any other process changes, the plant production capacity would have to be decreased by 20-30% to maintain the desired thermal treatment conditions.

To avoid the rate reduction from the energy input limitation, natural gas (or $C_1$ to $C_3$ fuel) is injected into the process at a 0.14:1 molar ratio with propylene. The energy no longer provided by the "impurities" in the propylene is replaced with energy from lower cost methane. This allows the plant to operate with a high purity feedstock while maintaining the operating rate, realizing a reduction in energy cost to operate the thermal treatment unit, and avoiding capital modification of thermal treatment unit.

Example 2

Characterization of Flammability Constraints on Exemplary and Comparative Processes One hazard inherent in the oxidation of propylene is the management of hazards associated with the flammability of propylene. This hazard can be managed by operating with a reactor feed composition outside of the flammable region by some margin of safety. The distance between the operating point and the flammable region is defined as the approach to the flammable limit. Margins of safety exist to cover error in flammable boundary correlations, errors in determination of reactor feed composition, and to prevent reactor trips associated with disturbances in reactor feed flows. The reactor feeds are manipulated such that the feed composition is moved above the upper flammable limit without passing through the flammable region. When one is above the flammable limit, increasing fuel content tends to increase the oxygen required to create a flammable mixture (more fuel increases the distance to the flammable limit). In a propylene partial oxidation process, propylene concentration cannot be increased independently because oxygen is required in a particular molar ratio (typically greater than 1.4:1) to propylene to complete the desired chemical reaction. Because of the oxygen to propylene constraint, the oxygen concentration must also increase when $C_3$ concentration increases. The net result of increasing propylene concentration at constant oxygen to propylene ratio is moving closer to the flammable region. A conventional two stage acrylic acid process with Absorber Off Gas recycle is operated with typical conditions, as recited in Table 2.

TABLE 2

Flammability Constraints on Exemplary and Comparative Processes

|  | Operation w/CGP | Operation w/PGP | Operation w/PGP + fuel injection |
|---|---|---|---|
| Relative $C_3H_6$ Rate (% of maximum) | 100 | 94.5 | 100 |
| $C_3H_6$ Purity (mol %) | 94.50 | 99.50 | 99.50 |
| $C_3H_6$ Concentration (mol %) | 7.7 | 7.4 | 7.7 |
| $C_3H_8$ Concentration (mol %) | 0.58 | 0.05 | 0.05 |
| Supplemental $C_1$-$C_3$ Fuel Concentration (mol %) | 0.00 | 0.00 | 1.28 |
| Total $C_1$-$C_3$ Fuel Concentration (mol %) | 0.58 | 0.05 | 1.33 |
| $C_3H_6$ Conversion (%) | 96.5 | 96.5 | 96.5 |
| Residual Acrolein Yield (%) | 1.00 | 1.00 | 1.00 |
| Total $C_1$-$C_3$ fuel:propylene (mol ratio) | 0.075 | 0.007 | 0.173 |
| AOG Heating Value (Btu/SCF) | 28 | 15 | 28 |
| Thermal Oxidizer Firebox Temperature (° C.) | 899 | 899 | 898 |
| Stack $O_2$ (mol %) | 2.1 | 2.1 | 2.1 |
| Tox Burner Capacity (%) | 70 | 100 | 70 |
| Approach to Flammable Limit | minimum | minimum | >minimum |
| Compressor Capacity (%) | 100 | 100 | 100 |

The results demonstrate that the process is simultaneously constrained by the ability of the compressor to pump mixed gas (air+recycle) to the reactor, the propylene concentration in the reactor feed, and the oxygen in the reactor outlet. Each one of these constraints represents a significant boundary. In turn, it is not possible to increase the capacity of a compressor without making capital investment. Operating too closely to the flammable region risks a process disturbance that could cause fire with significant safety and economic impact. If adequate excess oxygen is not maintained in the reactor outlet, it may cause the catalyst to age prematurely or cause incomplete conversion of acrolein to acrylic acid and high levels of acrolein fed to the thermal oxidizer.

Insufficient oxygen could potentially cause a release of acrolein if the thermal oxidizer is unable to handle the increased acrolein loading. Thus, in a process constrained as defined above and operated at the conditions defined above, the maximum operating rate has to be reduced by 5% (on propylene basis) when the propylene purity increases. By injecting natural gas into the propylene at 0.17:1 C1 to $C_3:C_3H_6$ molar ratio, the maximum rate can be maintained with higher purity of propylene. In addition, the "approach to flammability limit" is moved further away from the flammable region. The advantage of having an inert fuel present in the reactor is regained.

What is claimed is:

1. A process for preparing acrylic acid comprising:
   (1) preparing acrolein by catalytic gas phase oxidation comprising
       (a) providing a reaction gas comprising
           (i) 5 to 10 mol % propylene,
           (ii) 0.02 to 0.75 mol % propane, and
           (iii) 0.25 to 1.9 mol % of a fuel mixture comprising at least one of methane and ethane,
           wherein the molar ratio of the total amount of propane, methane, and ethane to the total amount of propylene is from 0.01:1 to 0.25:1;
       (b) contacting the reaction gas with a first mixed metal oxide catalyst to form a mixture comprising acrolein, wherein the first mixed metal oxide catalyst comprises one or more of molybdenum, bismuth, cobalt, and iron; and
   (2) contacting the acrolein mixture with a second mixed metal oxide catalyst to form a mixture comprising acrylic acid, wherein the second mixed metal oxide catalyst comprises one or more of molybdenum, vanadium, tungsten, copper, and antimony.

2. The process of claim 1, wherein the fuel mixture comprises methane.

3. The process of claim 1, wherein the reaction gas comprises propylene in an amount of from 7.5 to 8.2 mol %.

4. The process of claim 1, wherein the reaction gas comprises propane in an amount of from 0.03 to 0.62 mol %.

5. The process of claim 1, wherein the reaction gas comprises the fuel mixture in an amount of from 0.5 to 1.4 mol %.

6. The process of claim 2, wherein the reaction gas comprises methane in an amount of from 1.1 to 1.4 mol %.

7. The process of claim 1, wherein the molar ratio of the total amount of propane, methane, and ethane to the total amount of propylene is from 0.1:1 to 0.18:1.

8. The process of claim 1,
   wherein the first mixed metal oxide catalyst comprises a primary component selected from the group consisting of molybdenum, bismuth, and combinations thereof, and a secondary component selected from the group consisting of cobalt, iron, nickel, zinc, tungsten, phosphorous, manganese, potassium, magnesium, silicon, aluminum, and combinations thereof, wherein the primary component and secondary component are in an atomic ratio of from 9:28 to 28:9, and
   wherein the second mixed metal oxide catalyst comprises a primary component selected from the group consisting of molybdenum, vanadium, and combinations thereof, and a secondary component selected from the group consisting of tungsten, cobalt, copper, and combinations thereof, wherein the primary component and secondary component are in an atomic ratio of from 1:1 to 11:1.

9. The process of claim 1, wherein the fuel mixture comprises sulfur in an amount of less than 30 parts per million by volume of the fuel mixture.

10. A process for preparing acrylic acid comprising:
    (1) preparing acrolein by catalytic gas phase oxidation comprising
        (a) providing a reaction gas comprising
            (i) 7.5 to 8.2 mol % propylene,
            (ii) 0.03 to 0.62 mol % propane, and
            (iii) 0.5 to 1.4 mol % of a fuel mixture comprising at least one of methane and ethane, wherein the fuel mixture comprises sulfur in an amount of less than 30 parts per million by volume of the fuel mixture,
            wherein the molar ratio of the total amount of propane, methane, and ethane to the total amount of propylene is from 0.1:1 to 0.18:1; and
        (b) contacting the reaction gas with a first mixed metal oxide catalyst to form a mixture comprising acrolein, wherein the first mixed metal oxide catalyst comprises a primary component selected from the group consisting of molybdenum, bismuth, and combinations thereof, and a secondary component selected from the group consisting of cobalt, iron, nickel, zinc, tungsten, phosphorous, manganese, potassium, magnesium, silicon, aluminum, and combinations thereof, wherein the primary component and secondary component are in an atomic ratio of from 9:28 to 28:9; and
    (2) contacting the acrolein mixture with a second mixed metal oxide catalyst to form a mixture comprising acrylic acid, wherein the second mixed metal oxide catalyst comprises a primary component selected from the group consisting of molybdenum, vanadium, and combinations thereof, and a secondary component selected from the group consisting of tungsten, cobalt, copper, and combinations thereof, wherein the primary component and secondary component are in an atomic ratio of from 1:1 to 11:1.

* * * * *